US012745902B2

(12) United States Patent
Osman

(10) Patent No.: US 12,745,902 B2
(45) Date of Patent: Sep. 29, 2026

(54) VIDEO LARYNGOSCOPY APPARATUS

(71) Applicant: Ali Osman, Beaumont, TX (US)

(72) Inventor: Ali Osman, Beaumont, TX (US)

( * ) Notice: Subject to any disclaimer, the term of this patent is extended or adjusted under 35 U.S.C. 154(b) by 574 days.

(21) Appl. No.: 18/349,331

(22) Filed: Jul. 10, 2023

(65) Prior Publication Data

US 2024/0023801 A1 Jan. 25, 2024

Related U.S. Application Data

(60) Provisional application No. 63/391,581, filed on Jul. 22, 2022.

(51) Int. Cl.
*A61B 1/267* (2006.01)
*A61B 1/00* (2006.01)

(52) U.S. Cl.
CPC .......... *A61B 1/267* (2013.01); *A61B 1/00045* (2013.01); *A61B 1/00114* (2013.01)

(58) Field of Classification Search
CPC ...... A61B 1/267; A61B 1/2673; A61B 1/2676
See application file for complete search history.

(56) References Cited

U.S. PATENT DOCUMENTS 3,913,568 A 10/1975 Carpenter
5,584,795 A 12/1996 Valenti
6,174,281 B1 1/2001 Abramowitz
6,251,069 B1 6/2001 Mentzelopoulos et al.
7,214,184 B2 5/2007 McMorrow
8,460,184 B2 6/2013 Nearman et al.
8,814,787 B2 8/2014 Menegazzi
9,050,047 B2 * 6/2015 Chen ..................... A61B 1/267
9,167,962 B2 10/2015 Nearman et al.
9,326,669 B2 5/2016 Nearman et al.
9,332,896 B2 5/2016 Patel et al.
9,498,112 B1 11/2016 Stewart et al.
10,231,612 B2 3/2019 Nacouzi
10,299,668 B2 5/2019 Walk et al.
10,646,112 B2 5/2020 Nettelroth et al.
10,750,942 B2 8/2020 Aleckner (Continued)

FOREIGN PATENT DOCUMENTS

DE 29921801 U1 4/2000
FR 2821736 3/2001

*Primary Examiner* — Jan Christopher L Merene
(74) *Attorney, Agent, or Firm* — David Colls; Berger Singerman LLP

(57) ABSTRACT

A video laryngoscopy apparatus which facilitates selective depression of the epiglottis in the airway of a patient to facilitate unobstructed viewing of the vocal cords as well as ease in placement of an endotracheal tube in the patient's larynx during a video laryngoscopy procedure. The apparatus includes a head portion configured for attachment to a video laryngoscopy system. The apparatus includes a grip portion that extends from the head portion and an elongated, curved blade support segment that extends from the grip portion. A camera delimits the end of the blade support segment. The camera may functionally interface with the head portion to facilitate connection between the video cable and the camera system. The blade housing may extend from the blade support segment and include the blade that is coupled to a blade actuator that operably engages the blade to facilitate selective deployment of the blade.

19 Claims, 9 Drawing Sheets

(56) References Cited

U.S. PATENT DOCUMENTS

| | | | | |
|---|---|---|---|---|
| 10,799,104 | B2 | 10/2020 | Nagele | |
| 11,678,794 | B2 * | 6/2023 | Gerrans | A61B 1/0052 128/200.26 |
| 2007/0173697 | A1 | 7/2007 | Dutcher et al. | |
| 2008/0146880 | A1 | 6/2008 | Malek | |
| 2010/0261968 | A1 * | 10/2010 | Nearman | A61B 1/0004 600/196 |
| 2013/0310650 | A1 | 11/2013 | Hales et al. | |
| 2015/0099934 | A1 * | 4/2015 | Sartore | A61M 16/0486 600/187 |
| 2016/0095509 | A1 * | 4/2016 | Nacouzi | A61B 1/00105 600/193 |
| 2016/0256047 | A1 * | 9/2016 | Newcomb | A61B 1/0684 |
| 2018/0338675 | A1 * | 11/2018 | Eggli | A61B 1/267 |
| 2020/0015832 | A1 | 1/2020 | Levine et al. | |
| 2020/0054204 | A1 | 2/2020 | Attinger | |
| 2020/0253466 | A1 | 8/2020 | Clemente Pereira | |
| 2020/0345209 | A1 * | 11/2020 | Whitney | A61B 1/0052 |

* cited by examiner

VIDEO LARYNGOSCOPY APPARATUS

FIELD OF THE INVENTION

The present invention relates generally to laryngoscopy procedures, and more particularly, to a video laryngoscopy apparatus which facilitates selective depression of the epiglottis in the airway of a patient to facilitate unobstructed viewing of the vocal cords as well as ease in placement of an endotracheal tube in the patient's larynx by combining the "straightness" of a Miller blade with the curvature of a McIntosh blade during a video laryngoscopy procedure.

BACKGROUND OF THE INVENTION

Endotracheal intubation may be used in various medical conditions such as in application of general anesthesia, for example. Endotracheal intubation is carried out by insertion of an endotracheal tube into a patient's trachea to provide a conduit for introduction of oxygen into the airway of a patient. Improper placement of the endotracheal tube in the patient may lead to permanent neurological damage or death by causing inadequate ventilation. Accordingly, laryngoscopy is a procedure in which the trachea is viewed as an endotracheal tube is inserted in the patient's airway to ensure proper placement of the tube for adequate ventilation. During a laryngoscopy procedure, the tongue and other soft tissues may be moved out of the way to allow for visualization of vocal cords and the laryngeal aperture.

Video laryngoscopy is commonly used to facilitate endotracheal intubation. As compared to direct laryngoscopy, video laryngoscopy may offer superior views of the glottis (Cormack-Lehane I/II), higher intubation success rates for patients with anatomically difficult airways, particularly in obese patients and in patients in which the cervical spine is held in-line, as well as less spine movement and higher intubation success rates by inexperienced airway providers. Video laryngoscopy is touted as new standard of care for endotracheal intubation, as compared to direct laryngoscopy.

Laryngoscopy procedures may utilize a curved blade (knows as a "Mac" or "Macintosh" blade) or a straight blade (known as a "Miller" blade). In procedures in which the MacIntosh blade is used, the curved tip of the blade is placed in the epiglottic vallecula, which is the small mucosa-lined depression located at the base of the tongue just between the folds of the throat on either side of the median glossoepiglottic fold, during intubation. The blade lifts the tongue/epiglottis, and when the vocal cords in the larynx are visualized, then the endotracheal tube is passed through the larynx. The advantage of MacIntosh blade is that the tip of the blade sits in the vallecula and lifts the epiglottis indirectly by lifting the vallecula, thus providing an unobstructed view of vocal cords. Because the MacIntosh blade is curved, the endotracheal tube is easier to pass through the vocal cords. One drawback of the MacIntosh blade is that, since the blade does not directly lift the epiglottis, the vocal cords may not be visualized in some cases.

In procedures in which the straight Miller blade is used, the blade does not sit in the vallecula. Instead, the straight tip of the blade is designed to lift the epiglottis to provide visualization of the vocal cords. An advantage of using the Miller blade is that the blade directly lifts epiglottis, and thus, provides a less obstructed view of the vocal cords than procedures in which the MacIntosh blade is used. Since the anatomy of the mouth/larynx is curved, however, the endotracheal tube is configured to bend as it passes through the larynx. Therefore, because it is straight, the Miller blade renders it more difficult to pass the endotracheal tube during the intubation process. While the tip of the Miller blade directly lifts the epiglottis and enhances visibility of the vocal cords, the "straightness" of the Miller blade is disadvantageous when the endotracheal tube is passed through the larynx.

Accordingly, there is need for a video laryngoscopy apparatus which facilitates selective depression of the epiglottis in the airway of a patient to facilitate unobstructed viewing of the vocal cords as well as ease in placement of an endotracheal tube in the patient's larynx.

SUMMARY OF THE INVENTION

The present invention is directed to a video laryngoscopy apparatus which facilitates selective depression of the epiglottis in the airway of a patient to facilitate unobstructed viewing of the vocal cords as well as ease in placement of an endotracheal tube in the patient's larynx by combining the "straightness" of a Miller blade with the curvature of a McIntosh blade during a video laryngoscopy procedure by combining the "straightness" of a Miller blade with the curvature of a McIntosh blade during a video laryngoscopy procedure. The video laryngoscopy apparatus may include a head portion. The head portion may be configured for attachment to a video cable connected to a video monitor of a video laryngoscopy system. A grip portion may extend from the head portion. The grip portion may be selectively gripped by an operator of the apparatus during the procedure. An elongated, curved blade support segment may extend from the grip portion. A camera may terminate the blade support segment. The camera may functionally interface with the head portion to facilitate connection between the video cable and the camera. A blade housing may extend from the blade support segment. A blade may be positional in a stowed blade position in the blade housing and in a first extended blade position and a second extended blade position from the blade housing. A blade actuator may operably engage the blade to facilitate selective deployment of the blade in the stowed blade position, the first extended blade position and the second extended blade position.

In an exemplary application, the video laryngoscopy apparatus may be used to facilitate endotracheal intubation of a patient for establishment and maintenance of oxygen to the airway of the patient in any of various medical procedures. Accordingly, the head portion of the apparatus may be connected to the video monitor of the video laryngoscopy system typically via the video cable. An operator of the apparatus may grasp the grip portion. With the blade initially disposed in the stowed blade position in the blade housing, the blade support segment may be inserted through the oral cavity and into the throat of the patient until the blade housing is positioned in the epiglottic vallecula between the base of the tongue and the epiglottis. As it is inserted through the oral cavity and throat, the curvature of the blade support segment may substantially match or conform to the curvature of the patient's airway. The operator may then deploy the blade from the stowed blade position in the blade housing to the first extended blade position such that the blade extends from the blade housing proximal to the epiglottis of the patient. The operator may next deploy the blade from the first extended blade position to the second extended blade position such that the blade depresses the epiglottis against the base of the tongue to provide an unobstructed line of sight for the camera to the vocal cords of the patient and subsequently facilitate proper placement of an endotracheal tube through the vocal cords and larynx of the patient during an intubation procedure.

In an exemplary implementation of the invention, a video laryngoscopy apparatus which facilitates selective depression of the epiglottis to facilitate unobstructed viewing of the vocal cords as well as ease in placement of an endotracheal tube in the larynx by combining the "straightness" of a Miller blade with the curvature of a McIntosh blade during a video laryngoscopy procedure may include a head portion. The head portion may be configured for attachment to a video cable connected to a video monitor of a video laryngoscopy system. A user interface may be provided on the head portion. A grip portion may extend from the head portion. The grip portion may be selectively gripped by an operator of the apparatus during the procedure. An elongated, curved blade support segment may extend from the grip portion. A camera may terminate the blade support segment. The camera may functionally interface with the head portion to facilitate connection between the video cable and the camera. A blade housing may extend from the blade support segment. A blade may be positional in a stowed blade position in the blade housing and in a first extended blade position and a second extended blade position from the blade housing. A blade actuator may operably connect the user interface on the head portion with the blade to facilitate selective deployment of the blade in the stowed blade position, the first extended blade position and the second extended blade position. The user interface on the head portion may be manipulated by the operator to control the camera and the position of the blade.

In a second aspect, the head portion may include a head portion base. The grip portion may extend from the head portion base. A head portion body may extend from the head portion base opposite the grip portion. The user interface may be provided on the head portion body.

In another aspect, a cable port may be provided in the head portion body of the head portion. The cable port may be configured for connection to the video cable.

In another aspect, a cable port socket may be provided on the head portion body of the head portion. The cable port may be provided in the cable port socket.

In another aspect, the head portion body of the head portion may include a pair of spaced-apart side head portion surfaces, a rear head portion surface and a top head portion surface. The user interface may be provided on one or both side head portion surfaces. The cable port socket may be provided on the top head portion surface.

In another aspect, the user interface may include at least one manually manipulatable wheel, ball, knob, switch or handle which facilitates selective deployment of the blade in the stowed blade position, the first extended blade position and the second extended blade position.

In another aspect, the blade actuator may include a pulley mechanism, electric circuit and/or other mechanism suitable for facilitating actuation of the blade in the various blade positions responsive to manipulation or actuation of the user interface.

In another aspect, the user interface may include a blade position lock which can be actuated to lock the blade in the selected blade position.

In another aspect, the grip portion may include an elongated main grip portion segment having a proximal grip portion end at the head portion base of the head portion and a distal grip portion end opposite the proximal grip portion end.

In another aspect, the grip portion may have a frustoconical shape and may gradually narrow or taper from the proximal grip portion end to the distal grip portion end.

In another aspect, the grip portion may have a front grip surface and a rear grip surface which extend from the proximal grip portion end to the distal grip portion end.

In another aspect, the blade support segment may have a proximal blade support segment end at the distal grip portion end of the grip portion and a distal blade support segment end opposite the proximal blade support segment end.

In another aspect, the blade support segment may have a front blade support segment surface and a rear blade support segment surface extending from the front grip surface and the rear grip surface, respectively, of the grip portion.

In another aspect, the blade support segment may be flexible to match or conform to the curvature of the patient's airway.

In another aspect, at least one blade actuator opening may be provided in the distal blade support segment end of the blade support segment. The blade actuator may extend through the blade actuator opening and attach to the blade to facilitate actuation of the blade in the stowed blade position, the first extended blade position and the second extended blade position.

In another aspect, the blade housing may have a proximal housing end at the distal blade support segment end of the blade support segment and a distal housing end opposite the proximal housing end.

In another aspect, the blade housing may be elongated. In the stowed blade position, the blade may be disposed parallel to the longitudinal axis of the blade housing. In the first and second extended blade positions, the blade may be disposed at an angle to the longitudinal axis of the blade housing.

In another aspect, the blade housing may have a blade groove. In the stowed blade position, the blade may be disposed inside the blade groove. In the first and second extended blade positions, the blade may extend from the blade groove.

In another aspect, the blade housing may include a main housing segment. A side housing segment may extend from and along the main housing segment. The blade groove may be formed by and between the main housing segment and the side housing segment.

In another aspect, the blade may have a proximal blade end and a distal blade end opposite the proximal blade end. The blade actuator may operably engage the proximal blade end to facilitate selective deployment of the blade in the stowed blade position and in the first and second extended blade positions.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a video laryngoscopy apparatus which facilitates selective depression of the epiglottis in the airway of a patient to facilitate unobstructed viewing of the vocal cords as well as ease in placement of an endotracheal tube in the patient's larynx by combining the "straightness" of a Miller blade with the curvature of a McIntosh blade during a video laryngoscopy procedure by combining the "straightness" of a Miller blade with the curvature of a McIntosh blade during a video laryngoscopy procedure.

Figure 9:
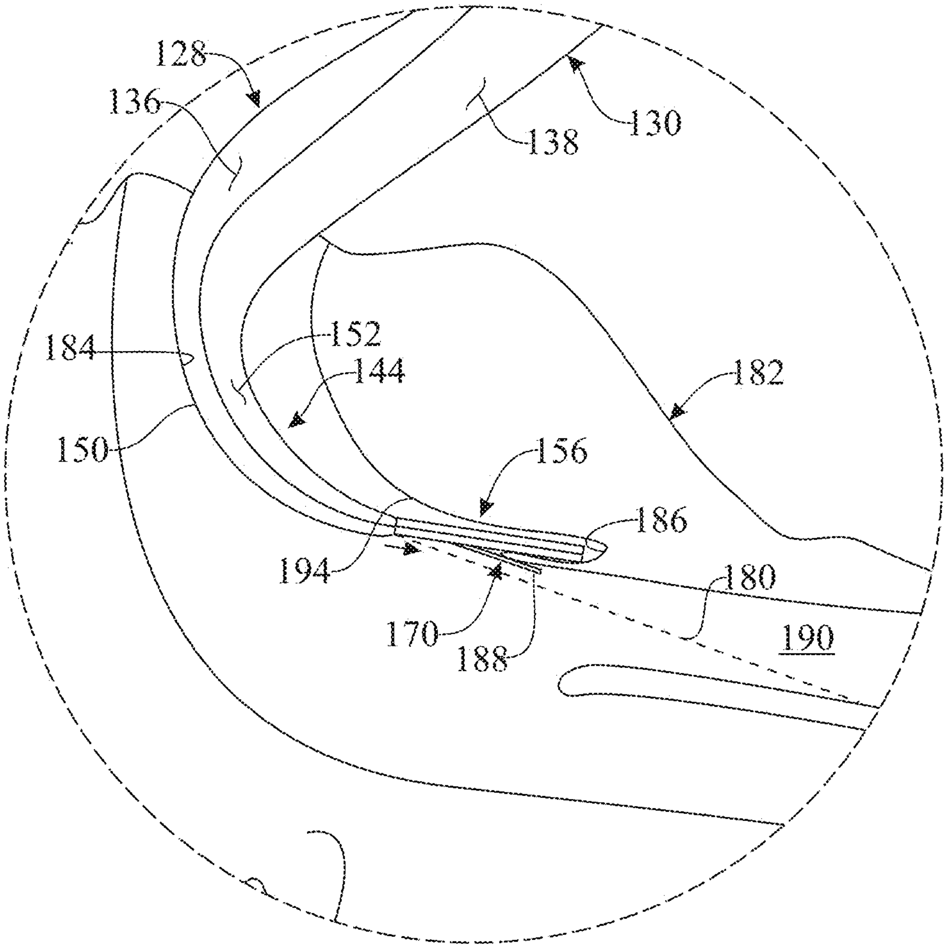
FIG. 9 is an enlarged sectional view of the blade support segment of the apparatus illustrated in FIG. 7, with the blade disposed in the second extended blade position and suppressing the epiglottis against the tongue of the patient to provide a clear line of sight for the camera on the apparatus into the larynx of the patient.
Figure 10:
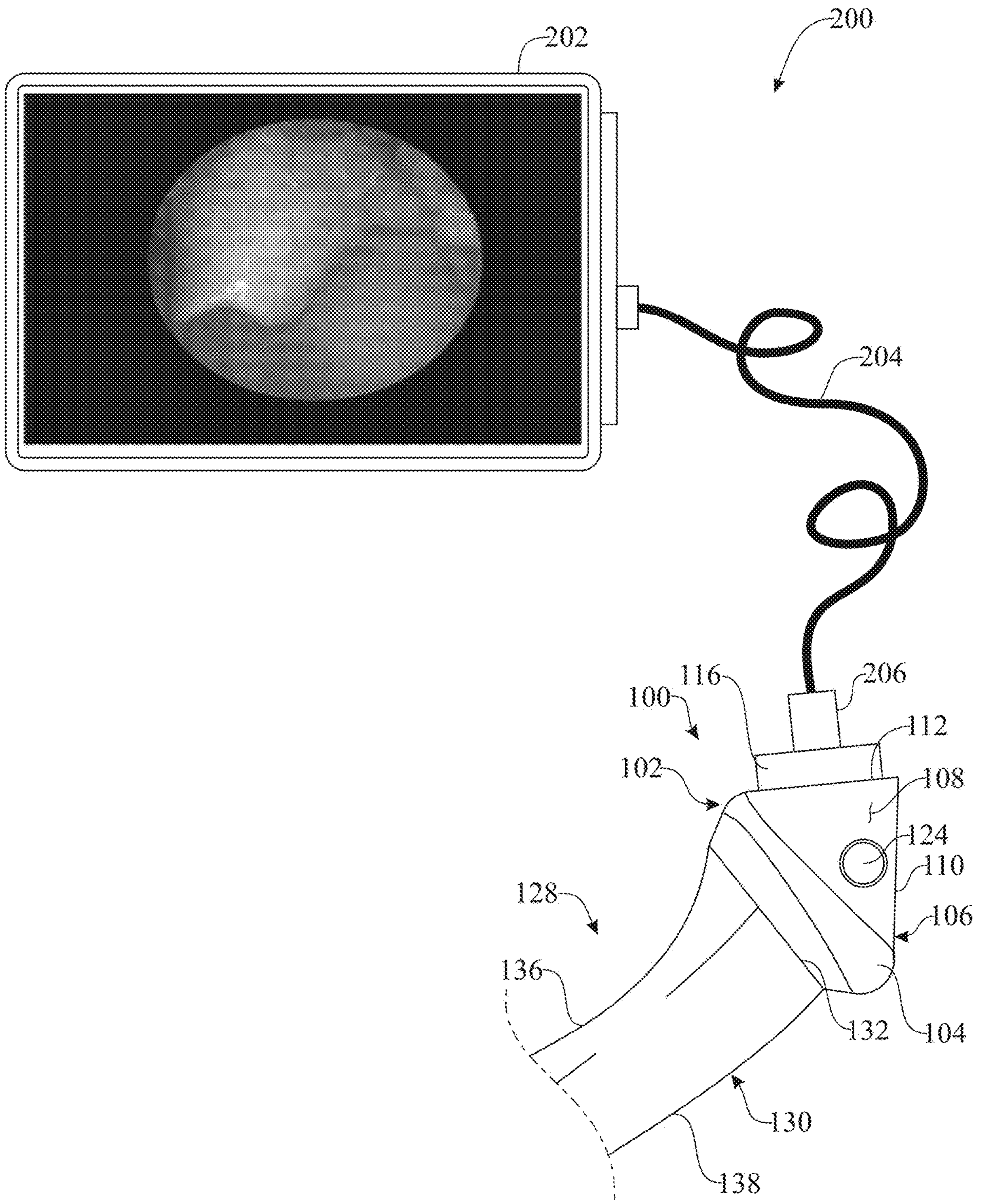
FIG. 10 is a sectioned side view of the head portion and a part of the grip portion of the apparatus, with the head portion connected to a video monitor of a video laryngoscopy system via a video cable and a laryngoscopy image displayed on the video monitor during a video laryngoscopy procedure carried out using the apparatus.

Referring initially to FIGS. 1-10, a video laryngoscopy apparatus, hereinafter apparatus 100, is illustrated in accordance with a first exemplary embodiment of the present invention. As shown for instance in FIG. 1, the apparatus 100 may include a head portion 102. As illustrated in FIG. 10, the head portion 102 may be configured for attachment to a video cable 204 connected to a video monitor 202 of a video laryngoscopy system 200. A grip portion 128 may extend from the head portion 102. The grip portion 128 may be selectively gripped by an operator (not illustrated) of the apparatus 100 during the laryngoscopy procedure.

Figure 3:
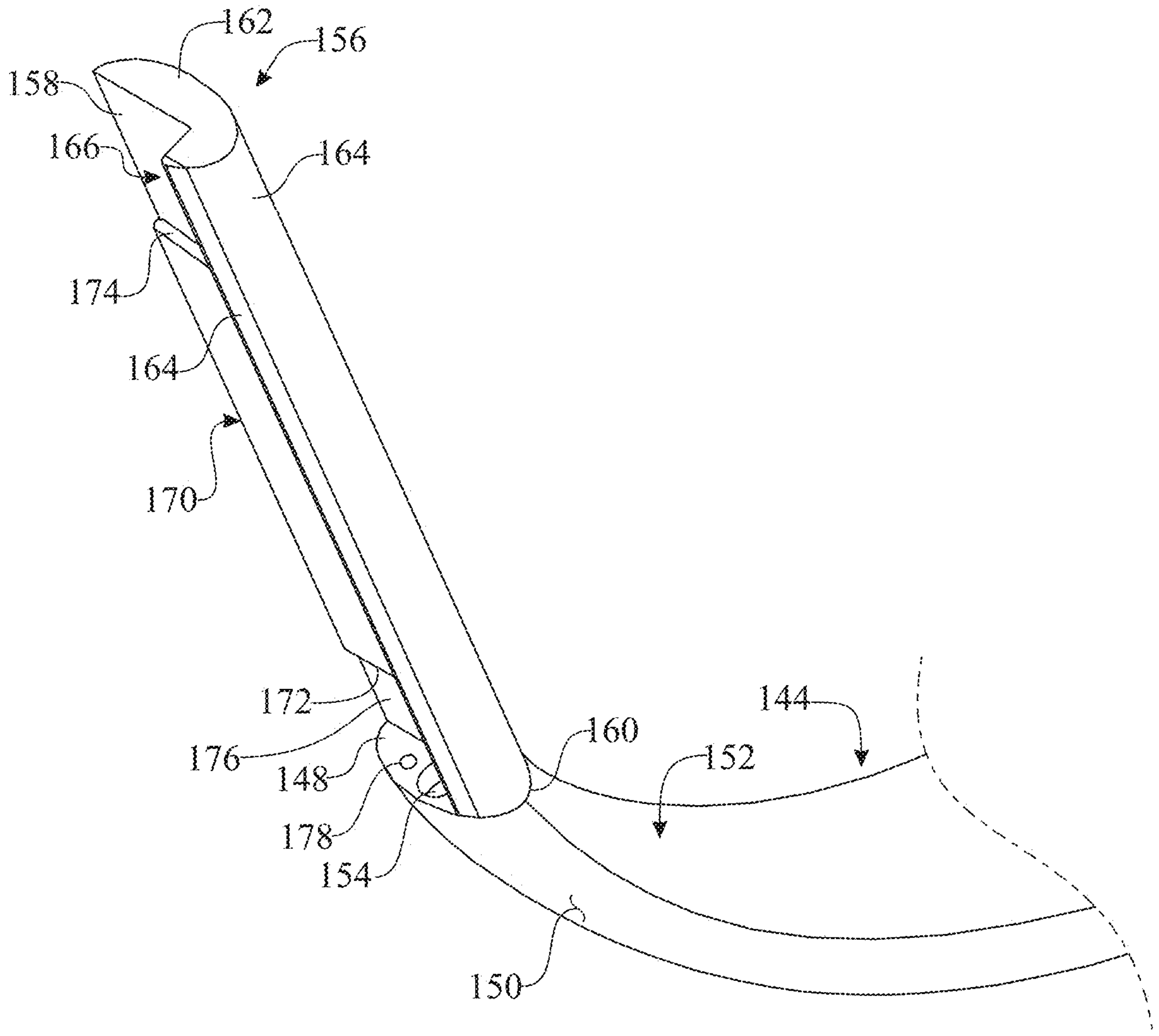
FIG. 3 presents a sectioned perspective view of a typical blade housing extending from the blade support segment of the apparatus, with the blade disposed in the stowed blade position in the blade housing.

An elongated, curved blade support segment 144 may extend from the grip portion 128. As illustrated in FIG. 3, a camera 178 may terminate the blade support segment 144. The camera 178 may functionally interface with the head portion 102 to facilitate connection between the video cable 204 and the camera 178, typically as will be hereinafter described.

A blade housing 156 may extend from the blade support segment 144. A blade 170 may be positional in a stowed blade position (FIG. 3) in the blade housing 156 and in a first extended blade position (illustrated in solid lines in FIG. 6) and a second extended blade position (illustrated in phantom lines in FIG. 6) from the blade housing 156. A blade actuator 176 (FIG. 3) may operably engage the blade 170 to facilitate selective deployment of the blade 170 in the stowed blade position, the first extended blade position and the second extended blade position.

A user interface 124 may be provided on the head portion 102. The blade actuator 176 may operably connect the user interface 124 on the head portion 102 with the blade 170 to facilitate selective deployment of the blade 170 in the stowed blade position, the first extended blade position and the second extended blade position. The user interface 124 on the head portion may be manipulated by the operator to control the camera 178 and the position of the blade 170.

Figure 1:
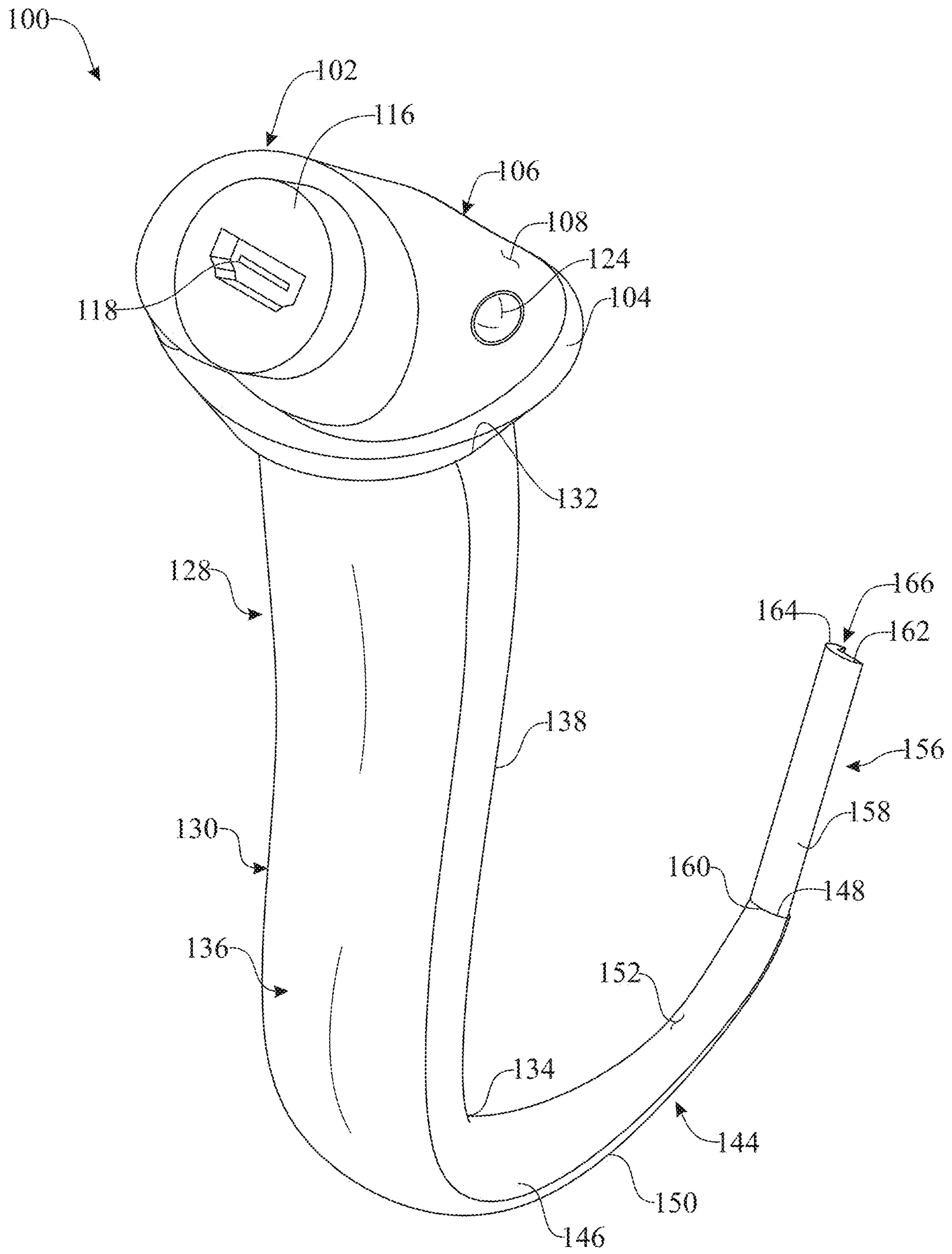
FIG. 1 presents an exploded front perspective view of a video laryngoscopy apparatus in accordance with an illustrative embodiment of the present invention.
Figure 2:
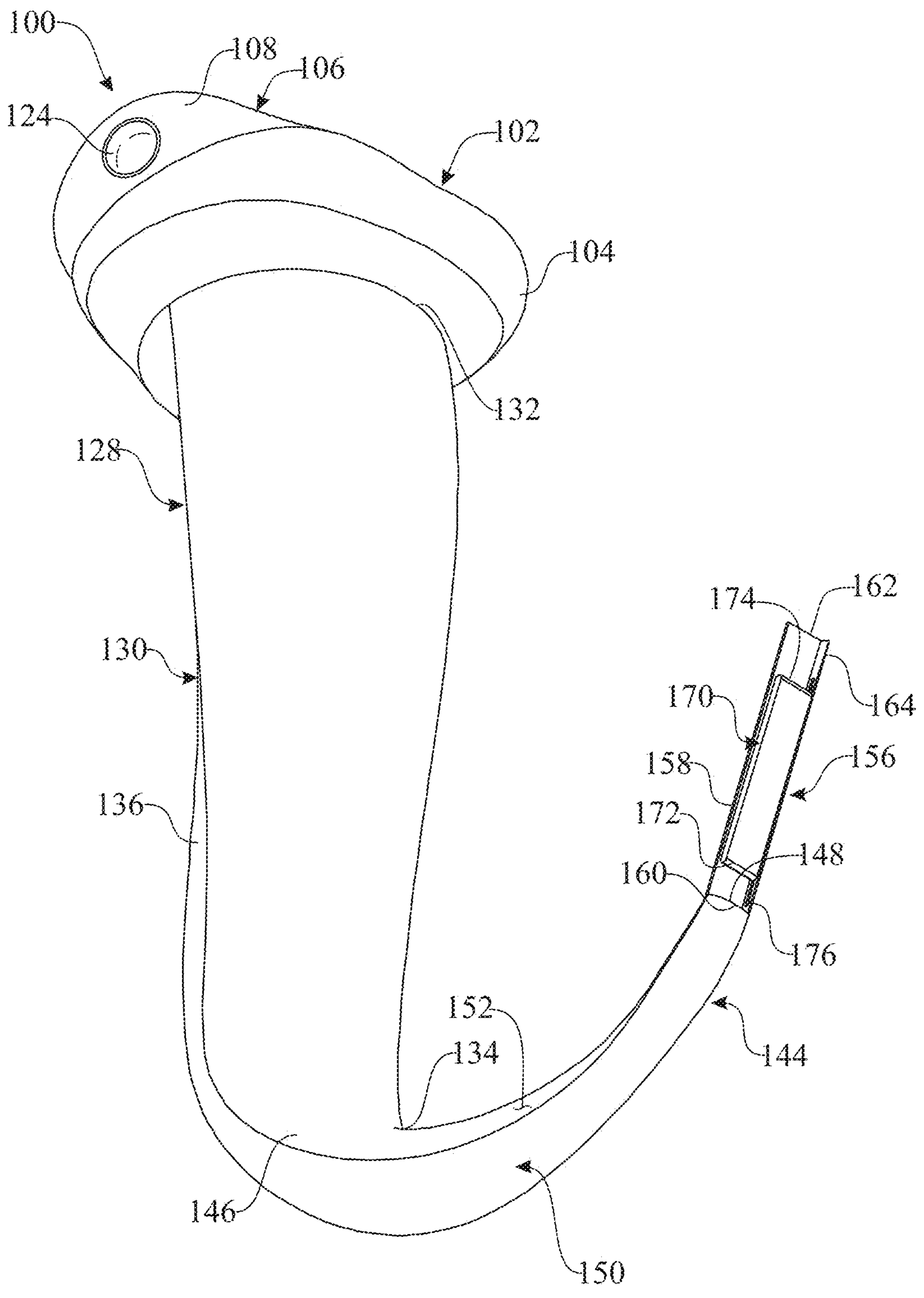
FIG. 2 presents a rear perspective view of the video laryngoscopy apparatus illustrated in FIG. 1.
Figure 4:
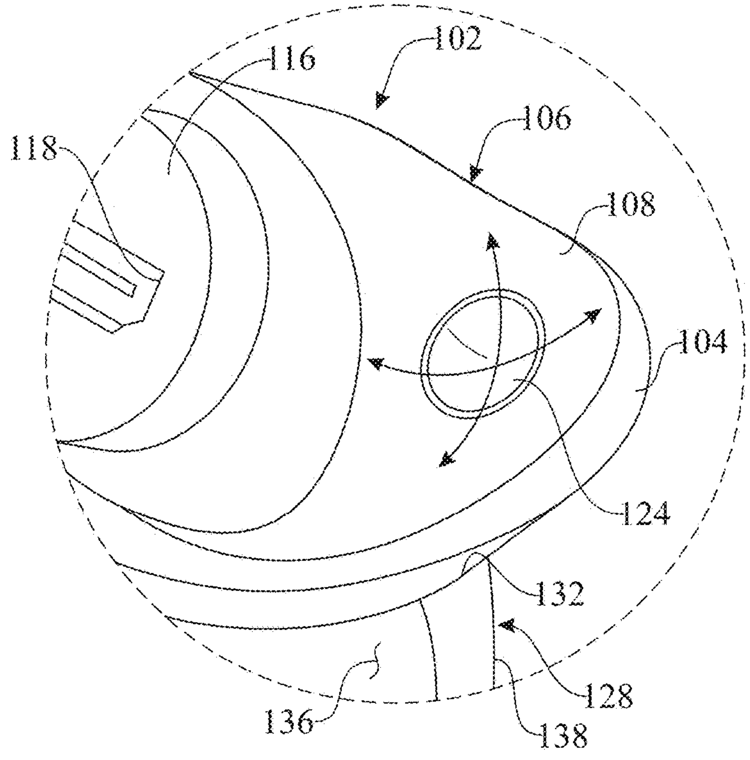
FIG. 4 presents a sectioned perspective view of the head portion of the apparatus and a typical user interface on the head portion.
Figure 5:
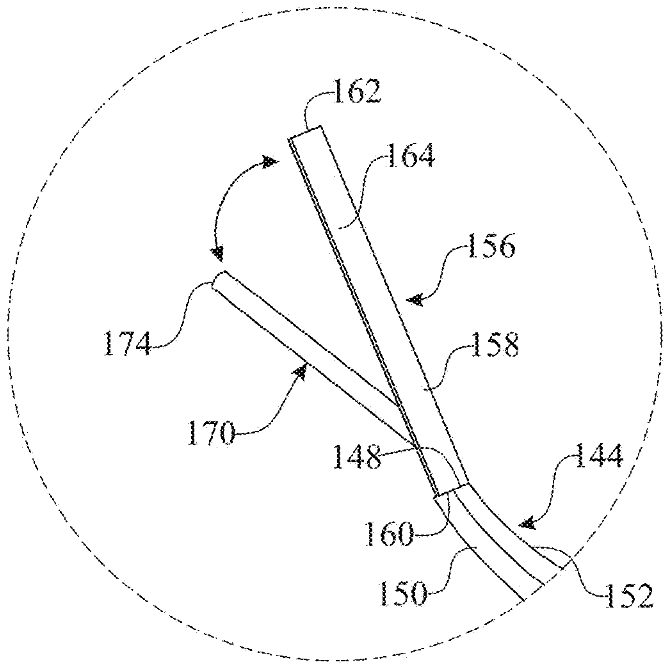
FIG. 5 presents a sectioned side view of the blade housing with the blade partially extended from the blade housing.
Figure 6:
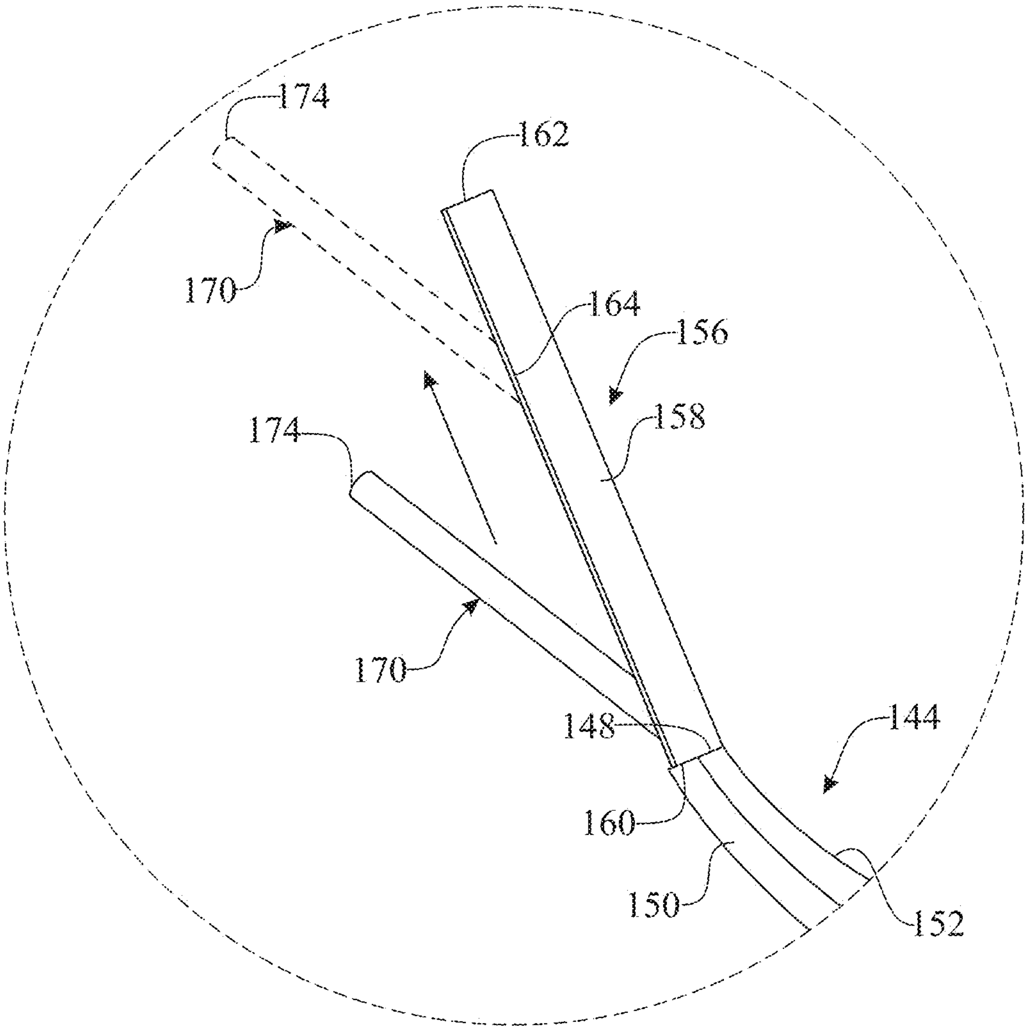
FIG. 6 presents a sectioned side view of the blade housing, more particularly illustrating typical deployment of the blade from the first extended blade position (illustrated in solid lines) to the second extended blade position (illustrated in phantom lines) from the blade housing.

In some embodiments, the head portion 102 may include a head portion base 104. The grip portion 128 may extend from the head portion base 104. A head portion body 106 may extend from the head portion base 104 opposite the grip portion 128. As illustrated in FIGS. 1, 2 and 4, the user interface 124 may be provided on the head portion body 106.

As illustrated in FIG. 1, a cable port 118 may be provided in the head portion body 106 of the head portion 102. The cable port 118 may be configured for connection to the video cable 204 (FIG. 10). In some embodiments, a cable port socket 116 may be provided on the head portion body 106 of the head portion 102. The cable port 118 may be provided in the cable port socket 116.

As particularly illustrated in FIG. 10, in some embodiments, the head portion body 106 of the head portion 102 may include a pair of spaced-apart side head portion surfaces 108 (one of which is illustrated). A rear head portion surface 110 and a top head portion surface 112 may extend between the side head portion surfaces 108. The user interface 124 may be provided on one or both side head portion surfaces 108. The cable port socket 116 may be provided on the top head portion surface 112.

The user interface 124 may include at least one manually manipulatable wheel, ball, knob, switch or handle which facilitates selective deployment of the blade 170 in the stowed blade position, the first extended blade position and the second extended blade position. In some embodiments, the user interface 124 may include a blade position lock (not illustrated) which can be actuated to lock the blade 170 in the selected blade position.

The blade actuator 176 may include any device or mechanism or combination thereof which facilitates actuation of the blade 170 in the various blade positions by selective manipulation of the user interface 124. For example and without limitation, the blade actuator 176 may include a pulley mechanism, electric circuit and/or other mechanism or combination thereof.

As particularly illustrated in FIGS. 1 and 2, in some embodiments, the grip portion 128 may include an elongated main grip portion segment 130 having a proximal grip portion end 132 at the head portion base 104 of the head portion 102 and a distal grip portion end 134 opposite the proximal grip portion end 132. The grip portion 128 may have a frustoconical shape and may gradually narrow or taper from the proximal grip portion end 132 to the distal grip portion end 134. In some embodiments, the grip portion 128 may have a front grip surface 136 and a rear grip surface 138 which extend from the proximal grip portion end 132 to the distal grip portion end 134.

As further illustrated in FIGS. 1 and 2, in some embodiments, the blade support segment 144 may have a proximal blade support segment end 146 at the distal grip portion end 134 of the grip portion 128 and a distal blade support segment end 148 opposite the proximal blade support segment end 146. A front blade support segment surface 150 and a rear blade support segment surface 152 may extend from the front grip surface 136 and the rear grip surface 138, respectively, of the grip portion 128. In some embodiments, the blade support segment 144 may be flexible according to the knowledge of those skilled in the art to match or conform to the curvature of the patient's airway.

As illustrated in FIG. 3, in some embodiments, at least one blade actuator opening 154 may be provided in the distal blade support segment end 148 of the blade support segment 144. One or more components of the blade actuator 176 may extend through the blade actuator opening 154 and attach to the blade 170 to facilitate actuation of the blade 170 in the stowed blade position, the first extended blade position and the second extended blade position.

As further illustrated in FIG. 3, in some embodiments, the blade housing 156 may have a proximal housing end 160 at the distal blade support segment end 148 of the blade support segment 144 and a distal housing end 162 opposite the proximal housing end 160. The blade housing 156 may be elongated. In the stowed blade position (FIG. 3), the blade 170 may be disposed parallel to the longitudinal axis of the blade housing 156. In the first and second extended blade positions (FIG. 6), the blade 170 may extend at an angle to the longitudinal axis of the blade housing 156.

As further illustrated in FIG. 3, the blade housing 156 may have a blade groove 166. In the stowed blade position, the blade 170 may be disposed inside the blade groove 166. In the first and second extended blade positions (FIG. 6), the blade 170 may extend from the blade groove 166. The blade groove 166 may longitudinally align or register with the front blade support segment surface 150 of the blade support segment 144.

In some embodiments, the blade housing 156 may include a main housing segment 158. A side housing segment 164 may extend from and along the main housing segment 158. The blade groove 166 may be formed by and between the main housing segment 158 and the side housing segment 164.

The blade 170 may be elongated with a proximal blade end 172 and a distal blade end 174 opposite the proximal blade end 172. The blade actuator 176 may operably engage the proximal blade end 172 of the blade 170 to facilitate selective deployment of the blade 170 in the stowed blade position and in the first and second extended blade positions.

In typical application, the apparatus 100 may be used to facilitate endotracheal intubation of a patient 182 for establishment and maintenance of oxygen to the airway of the patient 182 in any of various medical procedures. Accordingly, as illustrated in FIG. 10, the head portion 102 of the apparatus 100 may be connected to the video monitor 202 of the video laryngoscopy system 200 typically via the video cable 204. The video cable 204 may include a cable connector 206 which interfaces with the cable port 118 (FIG. 1) in the cable port socket 116 on the head portion 102.

An operator (not illustrated) of the apparatus 100 may grasp the grip portion 128. With the blade 170 initially disposed in the stowed blade position in the blade housing 156, as illustrated in FIG. 3, the blade support segment 144 may be inserted through the oral cavity 184 and into the throat of the patient 182 until the blade housing 156 is positioned in the epiglottic vallecula 186 between the base of the tongue 194 and the epiglottis 188. As it is inserted through the oral cavity 184 and throat, the curvature of the blade support segment 144 may substantially match or conform to the curvature of the patient's airway.

Figure 7:
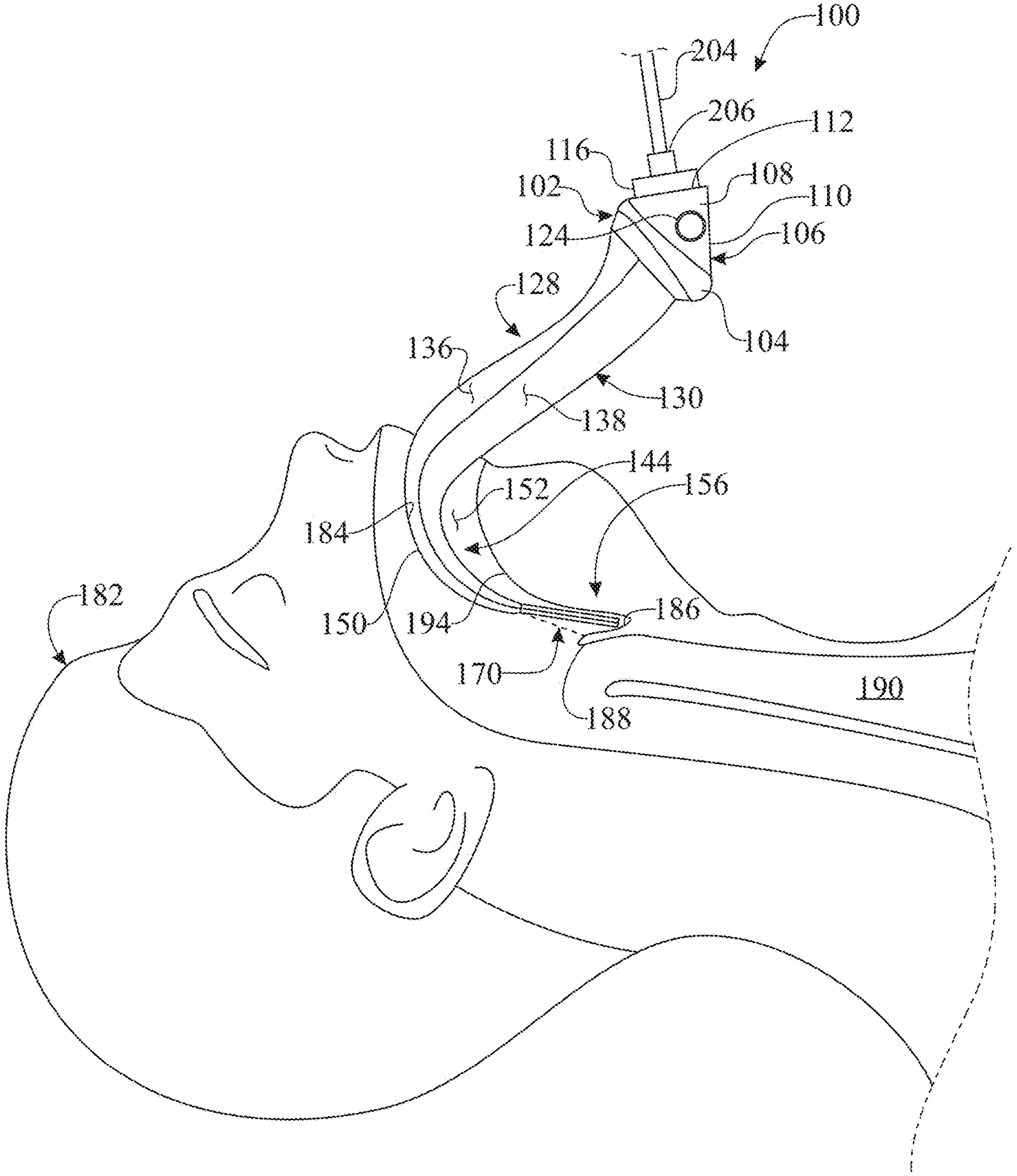
FIG. 7 is a cross-sectional view of the airway of a patient, with the blade support segment of the apparatus inserted through the oral cavity and into the throat of the patient and the blade housing seated in the epiglottic vallecula in typical application of the apparatus, with the blade in the stowed blade position in the blade housing.
Figure 8:
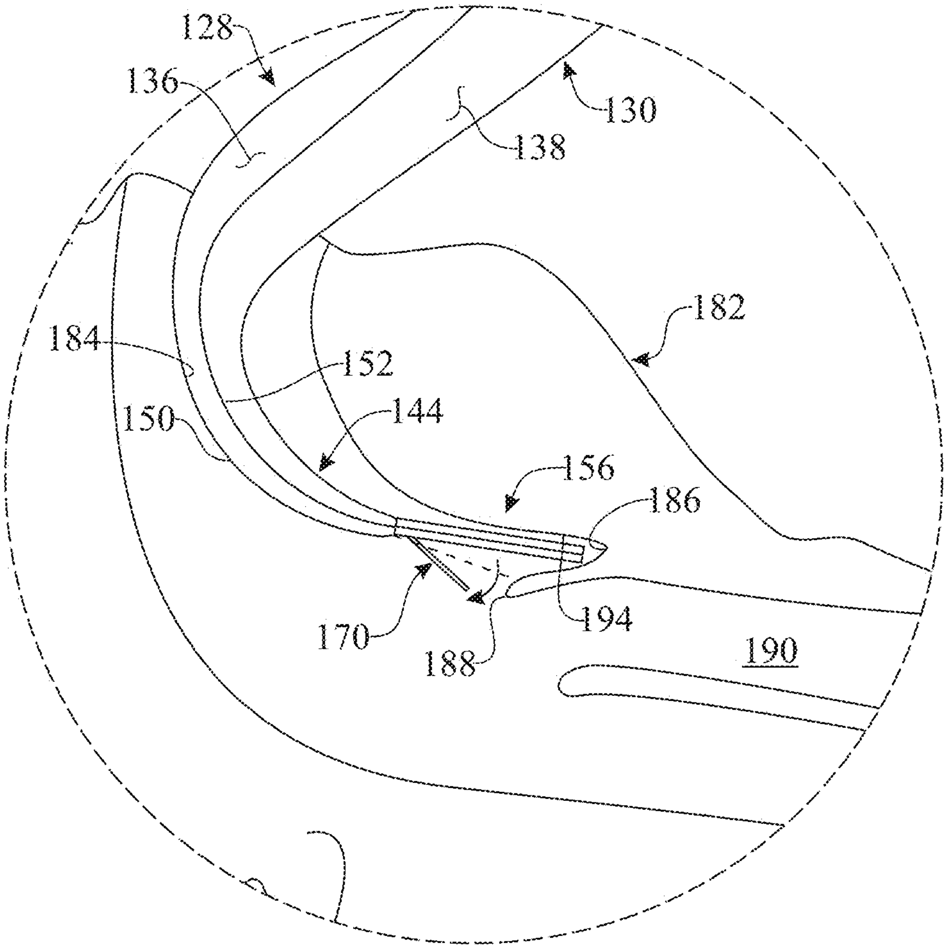
FIG. 8 is an enlarged sectional view of the blade support segment of the apparatus illustrated in FIG. 7, more particularly illustrating deployment of the blade from the stowed blade position to the first extended blade position.

As illustrated in FIG. 7, the operator of the apparatus 100 may then deploy the blade 170 from the stowed blade position in the blade housing 156 to the first extended blade position (FIG. 8) such that the blade 170 extends from the blade housing 156 proximal to the epiglottis 188 of the patient 182. As illustrated in FIG. 9, the operator may next deploy the blade 170 from the first extended blade position to the second extended blade position such that the blade 170 engages and depresses the epiglottis 188 against the main housing and towards the base of the tongue 194 to provide an unobstructed line of sight 180 for the camera 178 (FIG. 3) to the vocal cords of the patient 182 and subsequently facilitate proper placement of an endotracheal tube (not illustrated) through the vocal cords and larynx 190 of the patient 182 during an intubation procedure.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A video laryngoscopy apparatus which facilitates selective depression of the epiglottis in the airway of a patient to facilitate unobstructed viewing of the vocal cords and ease in placement of an endotracheal tube in the patient's larynx, comprising:

a head portion configured for attachment to a video cable connected to a video monitor of a video laryngoscopy system;

a grip portion extending from the head portion;

an elongated, curved blade support segment extending from the grip portion;

a camera terminating the blade support segment, the camera functionally interfacing with the head portion to facilitate connection between the video cable and the camera;

a substantially straight blade housing extending from the blade support segment;

a substantially straight blade positional in a stowed blade position in the blade housing and in a first extended blade position and a second extended blade position from the blade housing; and a mechanical or electrical blade actuator proximal to the substantially straight blade housing operably engaging the substantially straight blade, the blade actuator operable to facilitate selective deployment of the blade in the stowed blade position, the first extended blade position and the second extended blade position, wherein the substantially straight blade is configured to depress the epiglottis against the substantially straight blade housing.

2. The video laryngoscopy apparatus of claim 1, wherein the head portion includes a head portion base, the grip portion extending from the head portion base, a head portion body extending from the head portion base opposite the grip portion, and a user interface being provided on the head portion body.

3. The video laryngoscopy apparatus of claim 2, wherein a cable port is provided in the head portion body of the head portion.

4. The video laryngoscopy apparatus of claim 3, wherein a cable port socket is provided on the head portion body of the head portion, and further wherein the cable port is provided in the cable port socket.

5. The video laryngoscopy apparatus of claim 4, wherein the head portion body of the head portion includes a pair of spaced-apart side head portion surfaces, a rear head portion surface and a top head portion surface, and further wherein the user interface is provided on one or both side head portion surfaces and the cable port socket is provided on the top head portion surface.

6. The video laryngoscopy apparatus of claim 2, wherein the user interface includes at least one manually manipulatable wheel, ball, knob, switch or handle which facilitates selective deployment of the blade in the stowed blade position, the first extended blade position, and the second extended blade position.

7. The video laryngoscopy apparatus of claim 2, wherein the blade actuator includes a pulley mechanism and/or electric circuit suitable for facilitating actuation of the blade in the various blade positions responsive to manipulation or actuation of the user interface.

8. The video laryngoscopy apparatus of claim 2, wherein the grip portion includes an elongated main grip portion segment having a proximal grip portion end at the head portion base of the head portion and a distal grip portion end opposite the proximal grip portion end.

9. The video laryngoscopy apparatus of claim 8, wherein the grip portion has a frustoconical shape and gradually narrows or tapers from the proximal grip portion end to the distal grip portion end.

10. The video laryngoscopy apparatus of claim 8, wherein the grip portion includes a front grip surface and a rear grip surface which extend from the proximal grip portion end to the distal grip portion end.

11. The video laryngoscopy apparatus of claim 8, wherein the blade support segment has a proximal blade support segment end at the distal grip portion end of the grip portion and a distal blade support segment end opposite the proximal blade support segment end.

12. The video laryngoscopy apparatus of claim 10, wherein the blade support segment has a front blade support segment surface and a rear blade support segment surface extending from the front grip surface and the rear grip surface, respectively, of the grip portion.

13. The video laryngoscopy apparatus of claim 12, wherein the blade support segment is flexible to match or conform to the curvature of the patient's airway, and further wherein at least one blade actuator opening is provided in a distal blade support segment end of the blade support segment, the blade actuator extending through the blade actuator opening and attaching to the blade to facilitate actuation of the blade in the stowed blade position, the first extended blade position and the second extended blade position.

14. The video laryngoscopy apparatus of claim 8, wherein the blade housing has a proximal housing end at a distal blade support segment end of the blade support segment and a distal housing end opposite the proximal housing end, and further wherein the blade housing is elongated and in the stowed blade position, the blade is disposed parallel to a longitudinal axis of the blade housing and in the first and second extended blade positions, the blade is disposed at an angle to the longitudinal axis of the blade housing.

15. The video laryngoscopy apparatus of claim 1, wherein the blade housing has a blade groove and in the stowed blade position, the blade is disposed inside the blade groove and in the first and second extended blade positions, the blade extends from the blade groove.

16. The video laryngoscopy apparatus of claim 15, wherein the blade housing includes a main housing segment, a side housing segment extending from and along the main housing segment, and further wherein the blade groove is formed by and between the main housing segment and the side housing segment.

17. The video laryngoscopy apparatus of claim 1, wherein the blade has a proximal blade end and a distal blade end opposite the proximal blade end, the blade actuator operably engaging the proximal blade end to facilitate selective deployment of the blade in the stowed blade position and in the first and second extended blade positions.

18. A video laryngoscopy apparatus which facilitates selective depression of the epiglottis in the airway of a patient to facilitate unobstructed viewing of the vocal cords and ease in placement of an endotracheal tube in the patient's larynx, comprising:

a head portion configured for attachment to a video cable connected to a video monitor of a video laryngoscopy system;

a grip portion extending from the head portion for gripping by an operator of the apparatus;

an elongated, curved blade support segment extending from the grip portion;

a camera terminating the blade support segment, the camera functionally interfacing with the head portion to facilitate connection between the video cable and the camera;

a substantially straight blade housing extending from the blade support segment;

a substantially straight blade positional in a stowed blade position in the substantially straight blade housing and in a first extended blade position and a second extended blade position from the substantially straight blade housing; and a mechanical or electrical blade actuator proximal to the substantially straight blade housing operably engaging the substantially straight blade, the mechanical or electrical blade actuator operable to facilitate selective deployment of the substantially straight blade in the stowed blade position, the first extended blade position and the second extended blade position, wherein the head portion includes a head portion base, the grip portion extending from the head portion base, a head portion body extending from the head portion base opposite the grip portion, and a user interface being provided on the head portion body, wherein the substantially straight blade is configured to depress the epiglottis against a surface of the substantially straight blade housing, and wherein the mechanical or electrical actuator maintains the substantially straight blade in the stowed blade position until the substantially straight blade reaches the epiglottis.

19. A video laryngoscopy apparatus which facilitates selective depression of the epiglottis in the airway of a patient to facilitate unobstructed viewing of the vocal cords and ease in placement of an endotracheal tube in the patient's larynx, comprising:

a head portion configured for attachment to a video cable connected to a video monitor of a video laryngoscopy system;

a grip portion extending from the head portion for gripping by an operator of the apparatus, the head portion including a head portion base, the grip portion extending from the head portion base, a head portion body extending from the head portion base opposite the grip portion, and a user interface being provided on the head portion body;

an elongated, curved blade support segment extending from the grip portion;

a camera terminating the blade support segment, the camera functionally interfacing with the head portion to facilitate connection between the video cable and the camera;

a blade housing extending from the blade support segment and having a proximal housing end at a distal blade support segment end of the blade support segment and a distal housing end opposite the proximal housing end;

a blade positional in a stowed blade position in the blade housing and in a first extended blade position and a second extended blade position from the blade housing, wherein the blade housing is elongated and in the stowed blade position, the blade is disposed parallel to the longitudinal axis of the blade housing and in the first and second extended blade positions, the blade is disposed at an angle to the longitudinal axis of the blade housing; and a mechanical or electrical blade actuator proximal to the substantially straight blade housing operably engaging the blade, the blade actuator operable to facilitate selective deployment of the blade in the stowed blade position, the first extended blade position and the second extended blade position, wherein the user interface includes at least one manually manipulatable wheel, ball, knob, switch or handle which facilitates selective deployment of the blade in the stowed blade position, the first extended blade position, and the second extended blade position, and wherein the substantially straight blade is configured to depress the epiglottis against a surface of the substantially straight blade housing.

* * * * *